United States Patent [19]

Tsujino et al.

[11] 4,022,822

[45] May 10, 1977

[54] PROCESS FOR PREPARING SORBIC ACID

[75] Inventors: Yoshiaki Tsujino, Toyonaka; Masahiko Miyashita, Hirakata; Tokio Hashimoto, Ibaraki, all of Japan

[73] Assignee: Nippon Gohsei Kagaku Kogyo Kabushiki Kaisha, Osaka, Japan

[22] Filed: Apr. 22, 1975

[21] Appl. No.: 570,515

[30] Foreign Application Priority Data

Apr. 30, 1974 Japan .............................. 49-49310
Aug. 1, 1974 Japan .............................. 49-89228

[52] U.S. Cl. ...................... 260/526 N; 260/343.6
[51] Int. Cl.$^2$ ........................................ C07C 51/00
[58] Field of Search .............................. 260/526 N

[56] References Cited

UNITED STATES PATENTS 2,739,158  8/1953  Caldwell ...................... 260/526 N

FOREIGN PATENTS OR APPLICATIONS 1,300,458  6/1962  France ......................... 260/526 N

*Primary Examiner*—Vivian Garner
*Attorney, Agent, or Firm*—Armstrong, Nikaido & Marmelstein

[57] ABSTRACT

Novel process for preparing sorbic acid comprising contacting γ-vinyl-γ-butyrolactone with an acid such as mineral acids, sulfonic acids or halogenated carboxylic acids or a cation-exchange resin at a temperature of 30° to 150° C. Sorbic acid is economically prepared with ease and with simple procedures.

6 Claims, No Drawings

PROCESS FOR PREPARING SORBIC ACID

BACKGROUND OF THE INVENTION

The present invention relates to a novel process for preparing sorbic acid.

Sorbic acid and salts thereof have excellent antifungal activity and have been effectively employed as a preservative for foods. Sorbic acid is industrially manufactured by reacting crotonaldehyde with ketene to form polyester which can be converted to sorbic acid by heating or by means of acid, base or ion-exchange resin. However, such a process is not necessarily advantageous in point of its procedures or economy because the handling of polyester and the recovery or purification of sorbic acid are troublesome and also because of many process steps which require complicated process control.

OBJECTS OF THE INVENTION

It is an object of the present invention to provide a novel process for preparing sorbic acid.

A further object of the invention is to provide a process for economically preparing sorbic acid with simple procedures.

These and other objects of the invention will become apparent from the description hereinafter.

DETAILED DESCRIPTION

It has now been found that the above-mentioned objects can be accomplished by contacting γ-vinyl-γ-butyrolactone of the following formula:

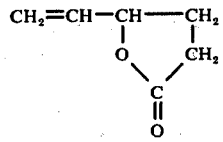

with an acid or a cation-exchange resin.

The process of the present invention is really novel and has never been found in any literatures. The starting material γ-vinyl-γ-butyrolactone can be readily produced from butadiene, obtainable at a lower price than crotonaldehyde and ketene, and its handling is easier than polyester since it can be purified by a simple procedure such as distillation. Further, according to the present invention, the preparation procedures are very simple because sorbic acid can be prepared by contacting γ-vinyl-γ-butyrolactone with an acid or a cation-exchange resin, and problems such as by-products, post-treatment and disposal of waste matter are reduced. Thus, the process of the present invention is of great advantage in industrially preparing sorbic acid.

In the present invention, γ-vinyl-γ-butyrolactone is employed as the starting material. The γ-vinyl-γ-butyrolactone is, for instance, readily produced by reacting butadiene with manganic acetate under pressure, but γ-vinyl-γ-butyrolactone employed in the present invention is not limited to that produced by such a process.

According to the present invention, sorbic acid is produced by contacting γ-vinyl-γ-butyrolactone with an acid or a cation-exchange resin. In carrying out the process of the invention, the contact is made in any of batchwise and continuous operations. In case of employing the acid, the acid may be added to γ-vinyl-γ-butyrolactone at once, continuously, or at intervals. In case of employing the cation-exchange resin, the lactone may be merely admixed with the resin in a vessel, or also be passed through a reaction tube charged with the resin.

In the invention, the acids and the cation-exchange resins employed are not particularly specified, and any acids and any cation-exchange resins can be employed. Examples of the acid preferably employed in the present invention are mineral acids such as hydrochloric acid, sulfuric acid, phosphoric acid and hydrogen chloride, aromatic sulfonic acids such as p-toluenesulfonic acid, benzenesulfonic acid and p-xylene-2-sulfonic acid, aliphatic sulfonic acids such as methanesulfonic acid, ethanesulfonic acid, propanesulfonic acid and butanesulfonic acid, and halogenated carboxylic acids such as trifluoroacetic acid, trichloroacetic acid and dichloroacetic acid. As the cation-exchange resins, any of strongly acidic cation-exchange resins such as sulfonic acid type resins and weakly acidic cation-exchange resins such as carboxylic acid type and phosphonic acid type resins are employed in the invention. Especially, strongly acidic cation-exchange resins are suitably employed. Practically, Amberlyst 15, Amberlyst XN-1004, Amberlite IR-120B, Amberlite IR-122, Amberlite IR-124, Amberlite IRC-84 (these are registered trademarks of Rohm & Haas Co.), Duolite C 20, Duolite C 10, Duolite CC 3 (these are registered trademarks of Chemical Process Co.), Dowex 50WX8, Dowex MSC-1 and Dowex CCR-2 (these are registered trademarks of Dow Chemical Co.) may be represented as examples.

The formation of sorbic acid occurs even at a normal temperature, but the heating is usually effected since the formation rate is accelerated. When the lactone is contacted with the acid, the acid is usually employed in an amount of 2 to 10 moles per mole of the lactone, and the contact of the lactone with the acid is carried out at a temperature of 30° to 150° C., preferably 70° to 110° for 30 minutes to 10 hours. When the lactone is contacted with the cation-exchange resin, the amount of the resin is not limited. The contact of the lactone with the resin is carried out at a temperature of 30° to 150° C., preferably 80° to 140° for 10 minutes to 5 hours.

Upon contacting the lactone with the acid, they may be contacted homogenously or heterogeneously. Solid acid can be contacted with γ-vinyl-γ-butyrolactone heterogenously. But in the process of manufacturing sorbic acid smoothly, there may be, if required, employed any of inert solvents which have no effect on forming sorbic acid and are able to dissolve the formed sorbic acid, for instance, carboxylic acids such as acetic acid, glacial acetic acid, propionic acid and butyric acid, esters thereof such as ethyl acetate, ethyl propionate and methyl butyrate, ethers such as diphenyl ether, dioxane and ethylene glycol diethyl ether, hydrocarbons such as petroleum distillate, isooctane, dodecane, dodecene and tetradecane, halogenated hydrocarbons such as carbon tetrachloride, dichlorododecane and 1,5-dibromopentane, ketones such as methyl ethyl ketone, acetophenone, cyclohexanone and sym-dichloroacetone, alcohols such as 2-ethylhexanol and n-decanol, and esters such as diethyl glutarate and ethyl acetoacetate. These inert solvents are able to dissolve sorbic acid. In case of employing the cation-exchange resin, the inert solvents not substantially dissolving the resin are selected. When the recovery and purification after the formation of sorbic acid are made by means of carrier distillation, the inert solvent having function as a carrier are advantageously selected.

After the conclusion of the formation, the formed sorbic acid is recovered from the reaction mixture. The crystals of sorbic acid are precipitated by cooling the reaction mixture which is, if desired, post-treated to filter the cation-exchange resin employed, or to remove by-products, or to distill off the inert solvent employed or unconverted lactone. Also, sorbic acid is distilled with the carrier such as petroleum distillate, dodecane or tetradecane and then separated from the carrier as crystals by cooling the distillate.

The sorbic acid so obtained is white crystals which are not colored. However, if desired, the crystals may be purified by recrystallization.

The present invention is more specifically described and explained by means of the following Examples.

EXAMPLE 1

[Preparation of γ-vinyl-γ-butyrolactone]

An autoclave equipped with a stirrer was charged with 570 ml. of acetic acid, 49 g. of potassium acetate, 86 g. of butadiene, and 230 g. of manganic triacetate, and the mixture was agitated at a temperature of 140° C., under pressure of 6.7 kg./cm.$^2$, for 3 hours. Then most of acetic acid in the reaction mixture was removed by distillation, and 200 ml. of water and 500 ml. of diethyl ether were added to the reaction mixture. From the ether layer, γ-vinyl-γ-butyrolacetone was extracted in yield of 56%. [Preparation of sorbic acid]

A one liter flask equipped with a stirrer was charged with 100 g. of γ-vinyl-γ-butyrolactone and 500 g. of hydrochloric acid in concentration of 36% by weight, and the mixture was agitated at a temperature of 90° C. for 7 hours to contact the lactone with hydrochloric acid. After removing a small quantity of black oily substance, the mixture was cooled to precipitate crystalline sorbic acid. Then, the crystals were filtered, and were washed with cold water and further with petroleum ether. The crystals were further dissolved in 2700 ml. of hot water and thereto 2.0 g. of active carbon was added. After filtering the active carbon, the crystals were recrystallized by cooling the filtrate. The yield of sorbic acid to γ-vinyl-γ-butyrolactone was 80%.

The obtained white crystals of sorbic acid had a melting point of 133° to 134° C. The infrared absorption and nuclear magnetic resonance spectrums of the obtained crystals agree with those of an authentic sorbic acid and it was confirmed that sorbic acid was obtained in high yield.

EXAMPLE 2

A one liter flask equipped with a stirrer was charged with 100 g. of γ-vinyl-γ-butyrolactone, 600 g. of isooctane, 30 g. of hydrochloric acid in concentration of 25% by weight and 1 g. of a surface active agent, and the mixture was vigorously agitated to form a uniform dispersion. After elevating temperature to 90° C., at this temperature the dispersion was further agitated for 8 hours to contact the lactone with hydrochloric acid. Then, the dispersion was allowed to stand to form two layers, a hydrochloric acid layer and an isooctane layer, and the hydrochloric acid layer was removed off. The isooctane layer was cooled to a room temperature and the precipitated white crystalline sorbic acid was filtered. The crystals were then washed with cold diethyl ester and dried. The yield of sorbic acid to γ-vinyl-γ-butyrolactone was 85%.

EXAMPLES 3 AND 4

The same procedures as in Example 1 were repeated except that 750 g. of sulfuric acid in concentration of 35% by weight (Example 3) and 460 g. of p-toluenesulfonic acid which was dissolved in 800 ml. of water (Example 4) were respectively employed instead of 500 g. of hydrochloric acid.

The similar results to Example 1 were obtained.

EXAMPLE 5

To 22.4 g. of γ-vinyl-γ-butyrolactone were added 12 g. of a strongly acidic styrene-type cation-exchange resin (commercially available under the registered trademark "Amberlyst XN-1004" made by Rohm & Haas Co. ) and 50 g. of glacial acetic acid, and admixed. The temperature was elevated to 115° C., and at this temperature the mixture was agitated for one hour to contact the lactone with the resin. After removing the cation-exchange resin by filtration, to the obtained mother liquor was added water in an amount of two times the amount of the mother liquor, and then cooled to precipitate white crystalline sorbic acid. The yield of the crystals to the lactone was about 86%.

The obtained white crystals had a melting point of 133° to 135° C. The infrared absorption and nuclear magnetic resonance spectrums of the obtained crystals agree with those of an authentic sorbic acid and it was confirmed that sorbic acid was prepared in high yield.

EXAMPLE 6

To 22.4 g. of γ-vinyl-γ-butyrolactone were added 15 g. of a strongly acidic styrene-type cation-exchange resin (commercially avilable under the registered trademark "Amberlyst 15" made by Rohm & Haas Co.) and 50 g. of a petroleum distillate (commercially available under the registered trademark "Isoper G" made by Esso Standard Petroleum Co., Ltd.) mainly consisting of hydrocarbons having 9 to 11 carbon atoms, and admixed. The mixture was agitated at a temperature of 130° C. for 30 minutes to contact the lactone with the resin. After filtering the cation-exchange resin, the obtained mother liquor was subjected to carrier distillation at a temperature of 150° to 165° C. under a pressure of 3 mmHg, supplying the petroleum distillate to the mother liquor, to give white crystalline sorbic acid. The yield of sorbic acid to the lactone was about 83%.

EXAMPLE 7

To 30 g. of γ-vinyl-γ-butyrolactone was added 7 g. of Amberlyst 15, and the mixture was agitated at a temperature of 120° C. till conversion of the lactone reached 30% by weight. After filtering the resin, the obtained mother liquor was cooled to precipitate white crystalline sorbic acid. The yield of sorbic acid to the consumed lactone was about 95%.

What we claim is:

1. A process for preparing sorbic acid which comprises contacting γ-vinyl-γ-butyrolactone with an acid selected from the group consisting of mineral acids, aromatic sulfonic acids, aliphatic sulfonic acids and halogenated carboxylic acids or an acidic cation-exchange resin at a temperature of 30° to 150° C and recovering the resulting sorbic acid.

2. The process of claim 1, wherein the γ-vinyl-γ-butyrolactone is contacted with the acid or the resin in the presence of an inert solvent.

3. The process of claim 2, wherein said inert solvent is a carboxylic acid selected from the group consisting of acetic acid, glacial acetic acid, propionic acid and butyric acid.

4. The process of claim 3, wherein said carboxylic acid is acetic acid or propionic acid.

5. The process of claim 2, wherein said inert solvent is a hydrocarbon selected from the group consisting of petroleum distillates which mainly consist of hydrocarbons having from 9 to 11 carbon atoms, isooctane, dodecane, dodecene and tetradecane.

6. The process of claim 5, wherein said hydrocarbon is petroleum distillate or isooctane.

* * * * *